US011414476B2

(12) United States Patent
Park et al.

(10) Patent No.: US 11,414,476 B2
(45) Date of Patent: Aug. 16, 2022

(54) METHOD FOR PRODUCING FUSION PROTEIN HAVING IGG FC DOMAIN (71) Applicant: ALTEOGEN, INC., Daejeon (KR)

(72) Inventors: Soon Jae Park, Daejeon (KR); Hye Shin Chung, Daejeon (KR); Sun Ah You, Daejeon (KR); Jeong Soo Cho, Daejeon (KR)

(73) Assignee: ALTEOGEN, INC., Daejeon (KR)

( * ) Notice: Subject to any disclaimer, the term of this patent is extended or adjusted under 35 U.S.C. 154(b) by 332 days.

(21) Appl. No.: 15/767,806

(22) PCT Filed: Oct. 14, 2016

(86) PCT No.: PCT/KR2016/011561
§ 371 (c)(1),
(2) Date: Apr. 12, 2018

(87) PCT Pub. No.: WO2017/065559
PCT Pub. Date: Apr. 20, 2017

(65) Prior Publication Data
US 2018/0298078 A1 Oct. 18, 2018

(30) Foreign Application Priority Data

Oct. 15, 2015 (KR) .................. 10-2015-0144330
Oct. 13, 2016 (KR) .................. 10-2016-0132633

(51) Int. Cl.
C12N 5/071 (2010.01)
C07K 14/71 (2006.01)
A61K 38/17 (2006.01)
C07K 19/00 (2006.01)

(52) U.S. Cl.
CPC ............ C07K 14/71 (2013.01); A61K 38/179 (2013.01); C07K 19/00 (2013.01); C12N 5/0682 (2013.01); C07K 2319/036 (2013.01); C07K 2319/30 (2013.01); C12N 2523/00 (2013.01)

(58) Field of Classification Search
CPC .. C07K 14/71; C07K 19/00; C07K 2319/036; C07K 2319/30; A61K 38/179; C12N 2523/00
See application file for complete search history.

(56) References Cited

U.S. PATENT DOCUMENTS

| 7,396,664 B2 * | 7/2008 | Daly | C07K 14/71 424/134.1 |
| 9,090,867 B2 | 7/2015 | Pla et al. | |
| 2002/0039580 A1 | 4/2002 | Browning et al. | |
| 2008/0269132 A1 | 10/2008 | Gomes et al. | |
| 2010/0331250 A1 | 12/2010 | Zhou et al. | |

FOREIGN PATENT DOCUMENTS

| JP | 2003501089 | 1/2003 |
| JP | 2010524503 | 7/2010 |
| JP | 2012/520661 | 9/2012 |
| JP | 2012-525415 | 10/2012 |
| JP | 2015526430 | 9/2015 |
| KR | 10-2014-0132016 | 11/2014 |
| RU | 2265661 | 12/2005 |
| RU | 2478702 | 4/2013 |
| WO | WO 2015/116315 | 8/2015 |
| WO | WO 2015186075 | 12/2015 |

OTHER PUBLICATIONS

Chakrabarti et al., Studies to prevent degradation of recombinant Fc-fusion protein expressed in mammalian cell line and protein characterization. International Journal of Molecular Science, vol. 17, No. 6 (2016) 913. (Year: 2016).*
Fan et al., Effect of culture temperature on TNFR-Fc productivity in recombinant glutamine synthetase-Chinese hamster ovary cells. Biotechnology Letters, vol. 32 (2010) pp. 1239-1244. (Year: 2010).*
R. Ian Freshney, "Quantitation." In: Culture of Animal Cell: A Manual of Basic Technique and Specialized Applications. (Hoboken, NJ, John Wiley & Sons, Inc., 2010), pp. 335-364. QH585.2.F74 2010. (Year: 2010).*
Estes et al., "Uncovering Methods for the Prevention of Protein Aggregation and Improvement of Product Quality in a Transient Expression System" Biotechnol. Prog. 2014, 1-10.
Galbraith et al., "Control of Culture Environment for Improved Polyethylenimine-Mediated Transient Production of Recombinant Monoclonal Antibodies by CHO Cells" Biotechnol. Prog. 2006, 22, 753-762.
Trummer et al., "Process Parameter Shifting: Part I. Effect of DOT, pH, and Temperature on the Performance of Epo-Fc Expressing CHO Cells Cultivated in Controlled Batch Bioreactors" Biotechnology and Bioengineering 2006,94 (6), 1033-1044.
Vázquez-Rey et al., "Aggregates in Monoclonal Antibody Manufacturing Processes" Biotechnology and Bioengineering 2011, 108 (7), 1494-1508.
Wulhfard et al., "Mild Hypothermia Improves Transient Gene Expression Yields Several Fold in Chinese Hamster Ovary Cells" Biotechnol. Prog. 2008, 24 (2), 458-465.
Zhu, "Mammalian cell protein expression for biopharmaceutical production" Biotechnology Advances 2012, 30, 1158-1170.

(Continued)

Primary Examiner — Kara D Johnson
(74) Attorney, Agent, or Firm — Norton Rose Fulbright US LLP (57) ABSTRACT The present invention relates to a method for preparing a fusion protein having an IgG Fc domain and, specifically, to a method for preparing a fusion protein having an IgG Fc domain, the method additionally comprising a step of culturing cells, which produce the fusion protein, at a decreased culture temperature, thereby increasing cell growth and cell viability so as to increase fusion protein productivity and inhibiting aggregate generation so as to improve quality and production yield.

14 Claims, 9 Drawing Sheets (56) References Cited

OTHER PUBLICATIONS

Chakrabarti, et al., "Studies to Prevent Degradation of Recombinant Fe-Fusion Protein Expressed in Mammalian Cell Line and Protein Characterization," *International Journal of Molecular Sciences*, 17(article 913), pp. 1-22. (2016).

Heroult, et al., "Heparin Affin Regulatory Peptide Binds to Vascular Endothelial Growth Factor (VEGF) and Inhibits VEGF-Induced Angiogenesis," *Oncogene*, 23, pp. 1745-1753. (2004).

International Search Report Issued in Corresponding PCT Application No. PCT/KR2016/011561, dated Jan. 24, 2017.

Kao & Puck, "Genetics of Somatic Mammalian Cells, VII. Induction and Isolation of Nutritional Mutants in Chinese Hamster Cells," *Proceedings of the National Academy of Sciences of the United States of America*, 60(4), pp. 1275-1281. (1968).

Kim, et al., "Intravitreal Anti-Vascular Endothelial Growth Factor Treatment for Retinal Diseases," *Journal of the Korean Medical Association*, 57(7), pp. 614-623. (2014).

Semeraro, et al., "Aflibercept in WetAMD: Specific Role and Optimal Use," *Drug Design, Development and Therapy*, 7, p. 711-722. (2013).

Sophie, et al., "Aflibercept: A Potent Vascular Endothelial Growth Factor Antagonist for Neovascular Age-Related Macular Degeneration and Other Retinal Vascular Diseases," *Biologics in Therapy*, 2(1), pp. 1-22. (2012).

Tseng, et al., "A Fusion Protein Composed of Receptor Binding Domain of Vascular Endolethial Growth Factor-A and Constant Region Fragment of Antibody: Angiogenesis Antagonistic Activity," *Cytotechnology*, 63, pp. 285-293. (2011).

Urlaub & Chasin, "Isolation of Chinese Hamster Cell Mutants Deficient in Dihydrofolate Reductase Activity," *Proceedings of the National Academy of Sciences of the United States of America*, 77(7), pp. 4216-4220. (1980).

Zhu, Jianwei, "Mammalian cell protein expression for biopharmaceutical production" *Biotechnology Advances* 2012, 30, 1158-1170.

Office Action issued in Corresponding Japanese Application No. 2020-082131, dated Jan. 11, 2022 (English Translation provided).

* cited by examiner

METHOD FOR PRODUCING FUSION PROTEIN HAVING IGG FC DOMAIN

CROSS-REFERENCE TO RELATED APPLICATIONS

The present application is a national phase application under 35 U.S.C. § 371 of International Application No. PCT/KR2016/011561, filed Oct. 14, 2016, which claims priority to and the benefit of Korean Patent Application Nos. 10-2015-0144330 and 10-2016-0132633 filed in the Korean Intellectual Property Office on Oct. 15, 2015 and Oct. 13, 2016, respectively, the disclosures of which are incorporated herein by reference in their entirety.

FIELD OF THE DISCLOSURE

The present invention relates to a method for producing a fusion protein having a human immunoglobulin G (IgG) Fc domain, particularly, a protein in which a soluble extracellular domain of a vascular endothelial growth factor (VEGF) receptor and a human immunoglobulin G (IgG) Fc domain are fused (for example, aflibercept).

DESCRIPTION OF RELATED ART

Vascular endothelial growth factor (VEGF) is an important factor which increases angiogenesis and vascular permeability. In particular, VEGF is overexpressed in tumor cells, and thus, promotes abnormal angiogenesis and tumor proliferation (Oncogene, 2004, 23, 1745-1753). Further, it is reported that abnormal angiogenesis is importantly related to other diseases in addition to tumorigenesis. In mechanisms through VEGF, abnormal angiogenesis is associated with wet macular degeneration, diabetic retinopathy, retinal vein occlusion macular edema, and the like, which are ophthalmic diseases (J. Korean Med. Assoc., 2014, 57, 7, 614-623).

As therapeutic agents for these ophthalmic diseases, pegaptanib (RNA aptamer), ranibizumab (monoclonal IgG antibody fragment (Fab)), and bevacizumab (monoclonal IgG antibody) have been used, and aflibercept (VEGFR1 and VEGFR2 fused with IgG1 Fc) was approved as a therapeutic agent for wet macular degeneration in the USA in 2011 (Biol. Ther., 2012, 2, 3, 1-22; Drug Design Development Therapy, 2013, 3, 7, 711-722).

Since the demand for these therapeutic recombinant proteins is increasing, much effort has been made to improve cell growth, viability, and protein production and quality by improving cell selection, medium optimization, and control of culture processes. Many proteins and polypeptides produced by cell culture are prepared by a method of producing cells by culturing them through a batch or fed-batch method at a predetermined temperature or pH for a predetermined time and then isolating the cells. Therefore, the production quantity and quality may be affected by cell culture conditions. There is a need for a method capable of preventing safety problems such as immunogenicity and the complication of purification processes in animal cell culture by increasing the amount of proteins produced, inhibiting generation of misfolded/aggregated proteins, or inhibiting deamidated bodies of proteins or substituted/deleted derivatives of amino acids from being generated, through adjustment and optimization of cell culture conditions related to production of proteins.

SUMMARY OF THE INVENTION

The present invention has been contrived to solve the aforementioned problems, and provides a method for producing an IgG Fc fusion protein for increasing an expression level of the protein.

Another object of the present invention is to provide a method for preparing a target protein, the method including: culturing cells producing the target protein, through the above-described production method.

Still another object of the present invention is to provide a pharmaceutical composition including a therapeutic protein prepared by the above-described preparation method and a pharmaceutically acceptable carrier.

However, technical problems to be solved by the present invention are not limited to the aforementioned problems, and other problems that are not mentioned may be clearly understood by a person skilled in the art from the following description.

In order to solve the above-described problems, it was confirmed that the present invention improved the productivity and quality of a fusion protein having an IgG Fc domain by optimizing culture conditions of cells which produce the fusion protein. Specifically, it was confirmed that by culturing the cells at a typical culture temperature (35.0° C. to 38.0° C.) for a predetermined time and then culturing the cells at a decreased culture temperature of 28.0° C. to 35.0° C., the productivity of the fusion protein was increased and the generation of aggregates of the fusion protein was inhibited, and the present invention was completed based on this fact.

In order to achieve the objects, the present invention provides a method for producing a protein in which a soluble extracellular domain of a vascular endothelial growth factor (VEGF) receptor and a human immunoglobulin G (IgG) Fc domain are fused, wherein cells are cultured at a decreased temperature of 28.0° C. or greater and less than 35.0° C. in order to increase an expression level of the fusion protein.

According to a preferred exemplary embodiment of the present invention, the fusion protein prepared by the method may be a fusion protein of which aggregates are decreased.

According to a preferred exemplary embodiment of the present invention, the cell culture may be large-scale cell culture.

According to another preferred exemplary embodiment of the present invention, the cell culture may be any one selected from the group consisting of batch culture, repeated batch culture, fed-batch culture, repeated fed-batch culture, continuous culture, and perfusion culture.

According to still another preferred exemplary embodiment of the present invention, the cell culture may be fed-batch cell culture.

According to yet another preferred exemplary embodiment of the present invention, the cell may be a mammalian cell.

According to yet another preferred exemplary embodiment of the present invention, the mammalian cell may be a CHO cell.

According to a yet another preferred exemplary embodiment of the present invention, the CHO cell may be a cell line of any one selected from the group consisting of DG44, DXB-11, K-1 and CHO-S.

According to yet another preferred exemplary embodiment of the present invention, a culture temperature from a culture initiation date until a temperature change may be a temperature included in a temperature range of 33.0° C. to less than 38.0° C.

According to yet another preferred exemplary embodiment of the present invention, the temperature may be lowered to 30.0° C. to 34.0° C.

According to yet another preferred exemplary embodiment of the present invention, a culture period from a culture initiation date until a temperature change may be 1 to 5 days.

According to yet another preferred exemplary embodiment of the present invention, a culture period after the temperature decrease may be 2 to 15 days.

According to a yet another exemplary embodiment of the present invention, in claim 1, a sum of the culture period before the temperature change and the culture period after the temperature change may be 3 days or more.

According to a yet another preferred exemplary embodiment of the present invention, the soluble extracellular domain of the VEGF receptor may include immunoglobulin-like domain 2 of a first VEGF receptor and immunoglobulin-like domain 3 of a second VEGF receptor.

According to a yet another preferred exemplary embodiment of the present invention, the produced protein may be a therapeutic protein.

The present invention also provides a method for preparing a target protein, the method including: culturing cells producing the target protein, through the above-described production method.

According to a preferred exemplary embodiment of the present invention, the method may additionally include a process of recovering the target protein from a culture broth in which cells, which produce the target protein, are cultured.

According to another preferred exemplary embodiment of the present invention, the target protein may be a therapeutic protein.

The present invention also provides a pharmaceutical composition including a therapeutic protein prepared by the above-described preparation method and a pharmaceutically acceptable carrier.

However, technical problems to be solved by the present invention are not limited to the aforementioned problems, and other problems that are not mentioned may be clearly understood by a person skilled in the art from the following description.

By additionally including a step of culturing cells producing a fusion protein having an IgG Fc domain at a decreased culture temperature, the present invention increases cell growth and cell viability, increases an expression level of the fusion protein, and inhibits aggregate generation, and as a result, fusion protein productivity is increased and quality is improved such that it is possible to prepare and supply the fusion protein in large amounts.

DETAILED DESCRIPTION OF THE INVENTION

Hereinafter, the present invention will be described in more detail.

As described above, much effort has been made to improve cell growth, viability, and protein production and quality by improving cell selection, medium optimization, and control of culture processes due to an increase in demand for therapeutic recombinant proteins, and there is a need for a method capable of preventing safety problems such as immunogenicity and the complication of purification processes in animal cell culture by increasing the amount of proteins produced, inhibiting generation of misfolded/aggregated proteins, or inhibiting deamidated bodies of proteins or substituted/deleted derivatives of amino acids from being generated, through adjustment and optimization of cell culture conditions related to production of proteins.

Thus, the present inventors have found a method to solve the above-described problems by confirming that the productivity of a fusion protein having an immunoglobulin G (IgG) Fc domain is increased and the generation of aggregates of the fusion protein is inhibited when cells were cultured at a typical culture temperature (35.0° C. to 38.0° C.) for a predetermined time and then at a decreased culture temperature of 28.0° C. to 35.0° C., and by providing a method for producing a fusion protein having an IgG Fc domain, in which the expression level of the protein in a cell culture is increased. By performing a step of culturing cells producing a fusion protein having an IgG Fc domain at a decreased culture temperature, the method for producing the fusion protein having the IgG Fc domain according to the present invention increases cell growth and cell viability, increases an expression level of the fusion protein, and inhibits aggregate generation, and as a result, fusion protein productivity is increased and quality is improved such that it is possible to prepare and supply the fusion protein in large amounts.

All the technical and scientific terms used in the present specification have the same meanings as those typically understood by a person skilled in the art to which the present invention pertains.

In the present invention, "a fusion protein having an IgG Fc domain" means a protein that binds to an Fc region which is a non-variable region of human IgG. In this case, in the present invention, "a protein" means a polymer of several or more amino acids linked by peptide bonds.

In the present invention, as the "amino acid polymer", human VEGF receptors 1 and 2 may be used, and preferably, extracellular domains of VEGF receptors 1 and 2 is used.

In the present invention, the "Fc region" is a non-variable region of an antibody, human IgG1, IgG2, IgG3, and IgG4 may be used, and preferably, an Fc region of IgG1 is used.

The present invention provides a method for producing a protein in which a soluble extracellular domain of a vascular endothelial growth factor (VEGF) receptor and a human IgG Fc domain are fused, wherein cells are cultured at a decreased temperature of 28.0° C. or greater and less than 35.0° C. in order to increase an expression level of the fusion protein.

In the method for producing the fused protein, the cell culture may be large-scale cell culture, and as a cell culture method, a typically used cell culture method may be used. For example, the cell culture method may be, but is not limited to, any one or more selected from the group consisting of batch culture, repeated batch culture, fed-batch culture, repeated fed-batch culture, continuous culture, and perfusion culture.

The "batch culture" is a culture method in which a small amount of seed culture broth is added to a medium and the cells are proliferated therein without adding a fresh medium thereto or discharging the culture broth during culturing. The "continuous culture" is a culture method in which a medium is continuously added and a culture broth is also continuously discharged during culturing. Further, a perfusion culture is also a type of continuous culture. Since the "fed-batch culture" is an intermediate between batch culture and continuous culture, the fed-batch culture is also called semi-batch culture, in which a medium is continuously or sequentially added during culturing, and the fed-batch culture is a culture method in which continuous discharging of the culture broth is carried out as in the continuous culture, but cells do not flow out. In the present invention, any of the above-described culture methods may be used, preferably, fed-batch culture or continuous culture is used, and particularly preferably, fed-batch culture is used.

In the present invention, for the expression of the Fc fusion protein, any type of cell may be used without limitation as long as the cell is a stable cell line capable of constantly expressing the fusion protein, and preferably, the cell is a mammalian cell. More preferably, a generally used animal culture cell such as a CHO cell, a HEK cell, a COS cell, a 3T3 cell, a myeloma cell, a BHK cell, a HeLa cell, or a Vero cell is used, and particularly, a CHO cell is preferred when the cell is used for the purpose of expressing the Fc fusion protein in a large amount. Further, in order to prepare a desired protein, particularly preferred is a cell suitable for introducing a desired gene, such as a dhfr-CHO cell (Proc. Natl. Acad. Sci. USA, 1980, 77, 4216-4220) which is a CHO cell lacking a DHFR gene, or a CHO K-1 cell (Proc. Natl. Acad. Sci. USA, 1968, 60, 1275). As the CHO cell, particularly, a DG44 cell line, DXB-11 cell line, K-1 cell line or CHO-S cell line is preferred, the K-1 cell line is particularly preferred, and the introduction of a vector into a host cell may be implemented by a method such as a calcium phosphate method, a DEAE dextran method, an electroporation method, or lipofection.

In the method for producing a protein in which a soluble extracellular domain of a VEGF receptor and a human IgG Fc domain are fused according to the present invention, as the temperature at which culture is carried out from initiation until a temperature change, a temperature typically used for culturing may be selected according to the type of cell. For example, a temperature range typically used to culture mammalian cells may be 33.0° C. to less than 38.0° C., and particularly preferably 37.0° C. In a preferred exemplary embodiment of the present invention, cells that overexpress recombinant aflibercept were cultured at 37.0° C. from the culture initiation date until the temperature change.

In the present invention, the timing for the temperature change is determined by an expression level of a target protein. Specifically, an optimal timing for the temperature change may be determined by performing an experiment shown in Example 3, but since the final cell densities are different depending on the types of cells or culture conditions used, a final cell density of about $1 \times 10^6$ cells/ml to about $1 \times 10^8$ cells/ml is generally preferred.

The present invention provides a method for increasing productivity per cell and inhibiting aggregate generation when a CHO cell into which a gene encoding a protein is introduced is cultured for the purpose of preparing the fusion protein, in which the cell is cultured at a typical culture temperature from a culture initiation date for 1 day to 5 days, and then the culture temperature is decreased. The period after the temperature is changed until the culture is terminated may be generally 1 day to 30 days, and preferably 2 days to 15 days. The sum of the culture period before the temperature change and the culture period after the temperature change may be 3 days or more. Specifically, the method for producing the fusion protein by culturing cells producing the fusion protein is characterized by culturing the cells at a typical culture temperature for a predetermined time, and then continuously culturing the cells at a decreased temperature. Here, the typical culture temperature is generally 33.0° C. to 38.0° C., which is a temperature suitable for the cell proliferation of cells derived from a homeothermic animal, and is most generally 37.0° C.

In the method for producing a protein in which a soluble extracellular domain of a VEGF receptor and a human IgG Fc domain are fused according to the present invention, a decreased culture temperature means a temperature range lower than a typical culture temperature, and an optimally decreased culture temperature is determined according to an expression level of a target protein. Accordingly, in the present invention, an experiment was performed as described in Example 2 to derive an optimally decreased culture temperature range in which a target protein is maximally expressed. Although an optimally changed temperature may be found through the experiment as in Example 2, since the final cell densities are different depending on the type or culture condition of cell, the optimally decreased culture temperature may be preferably 28.0° C. to 35.0° C., and more preferably 30.0° C. to 34.0° C.

In the method for producing a protein in which a soluble extracellular domain of a VEGF receptor and a human IgG Fc domain are fused according to the present invention, the soluble extracellular domain of the VEGF receptor may include immunoglobulin-like domain 2 of a first VEGF receptor and immunoglobulin-like domain 3 of a second VEGF receptor. Specifically, the protein produced by the production method of the present invention may be a therapeutic protein.

In a preferred exemplary embodiment of the present invention, the culture temperature from the culture initiation date until the temperature change was set to 37.0° C. to culture cells, which overexpress recombinant aflibercept, for 3 days until the density of cells in a flask reached $8\times10^6$ cells/ml. Thereafter, the cells were fed-batch cultured according to the supply schedule in Table 1 at a decreased culture temperature of 32.0° C.

Figure 1:
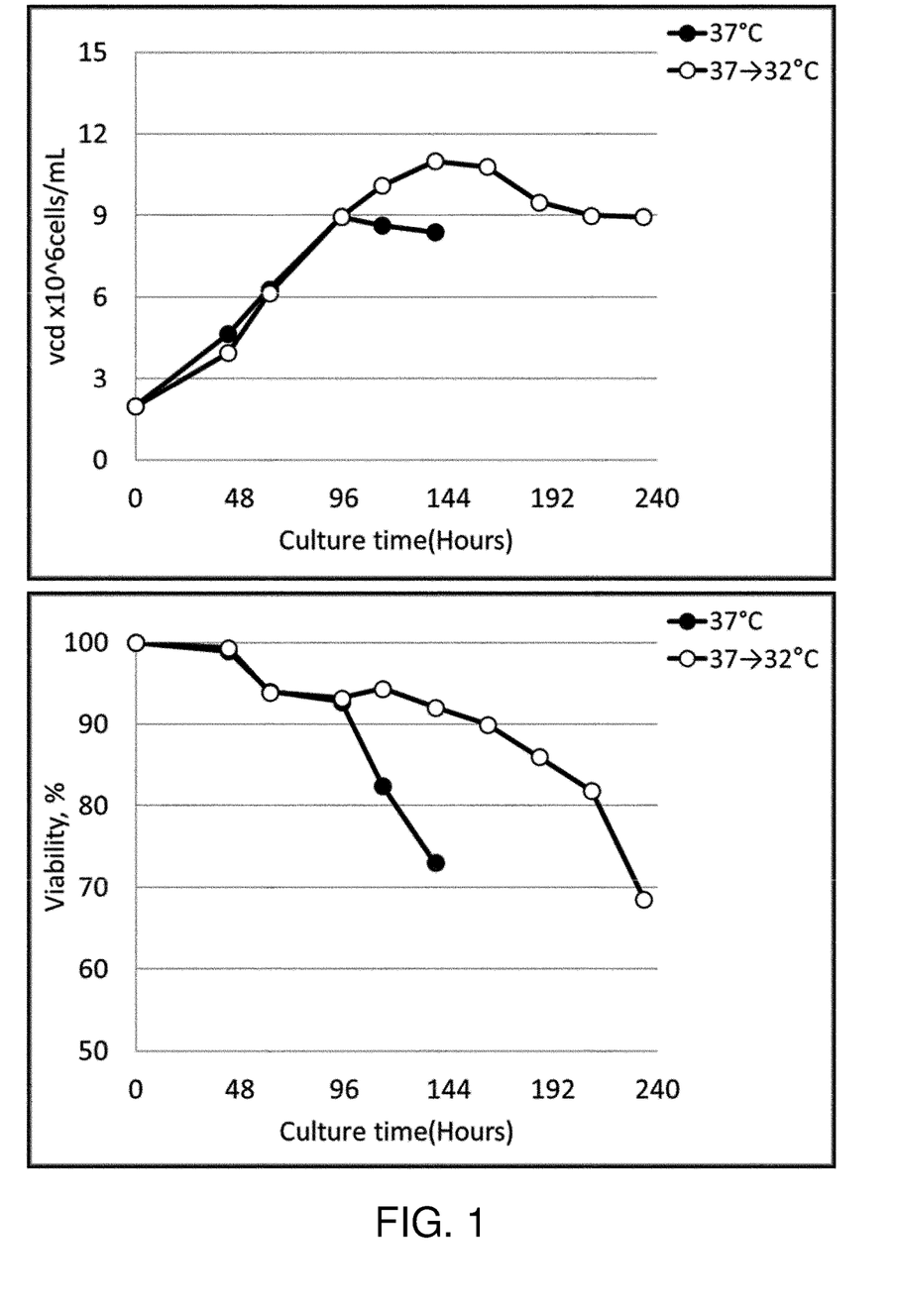
FIG. 1 is a graph analyzing a change in cell growth and cell viability according to the culture temperature of cells producing aflibercept.
Figure 2:
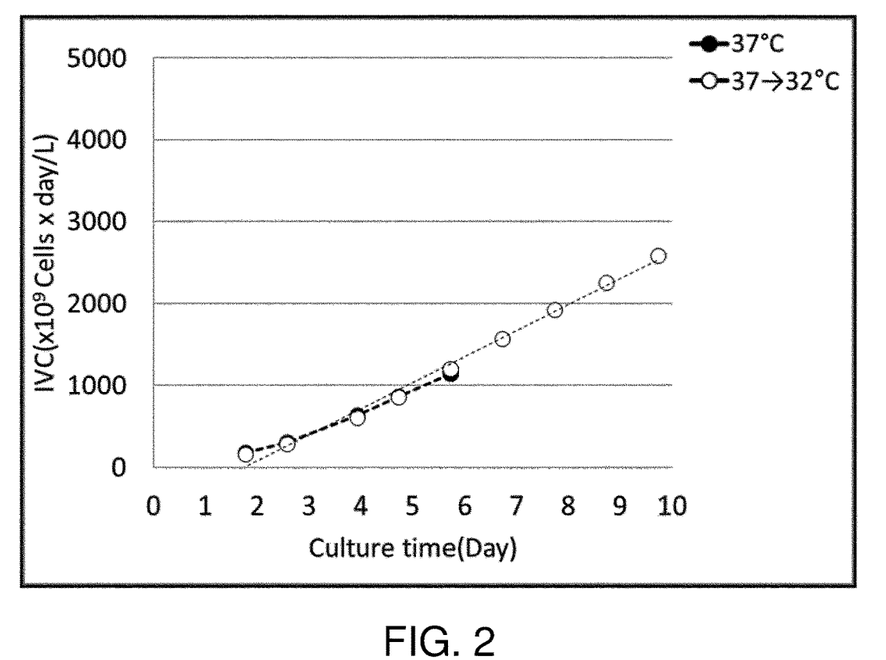
FIG. 2 is a graph showing integrated viable cell numbers (Y-axis; IVC [normalized $10^9$ cells×day/L]) producing aflibercept, normalized to IVC, over time (X-axis; culture time [day]).
Figure 3:
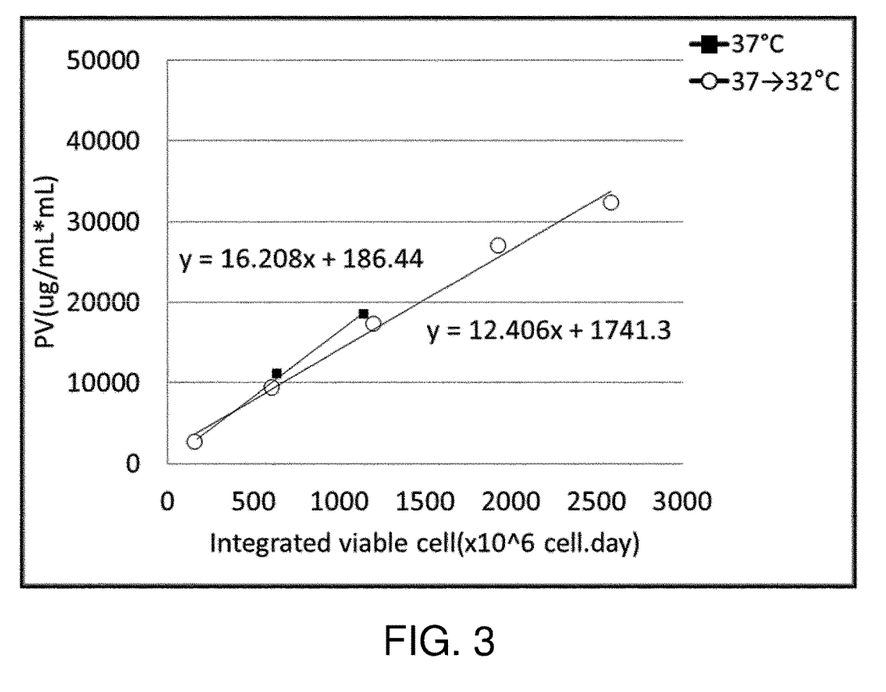
FIG. 3 is a graph showing a change in specific production rate according to the culture temperature of cells producing aflibercept.
Figure 4:
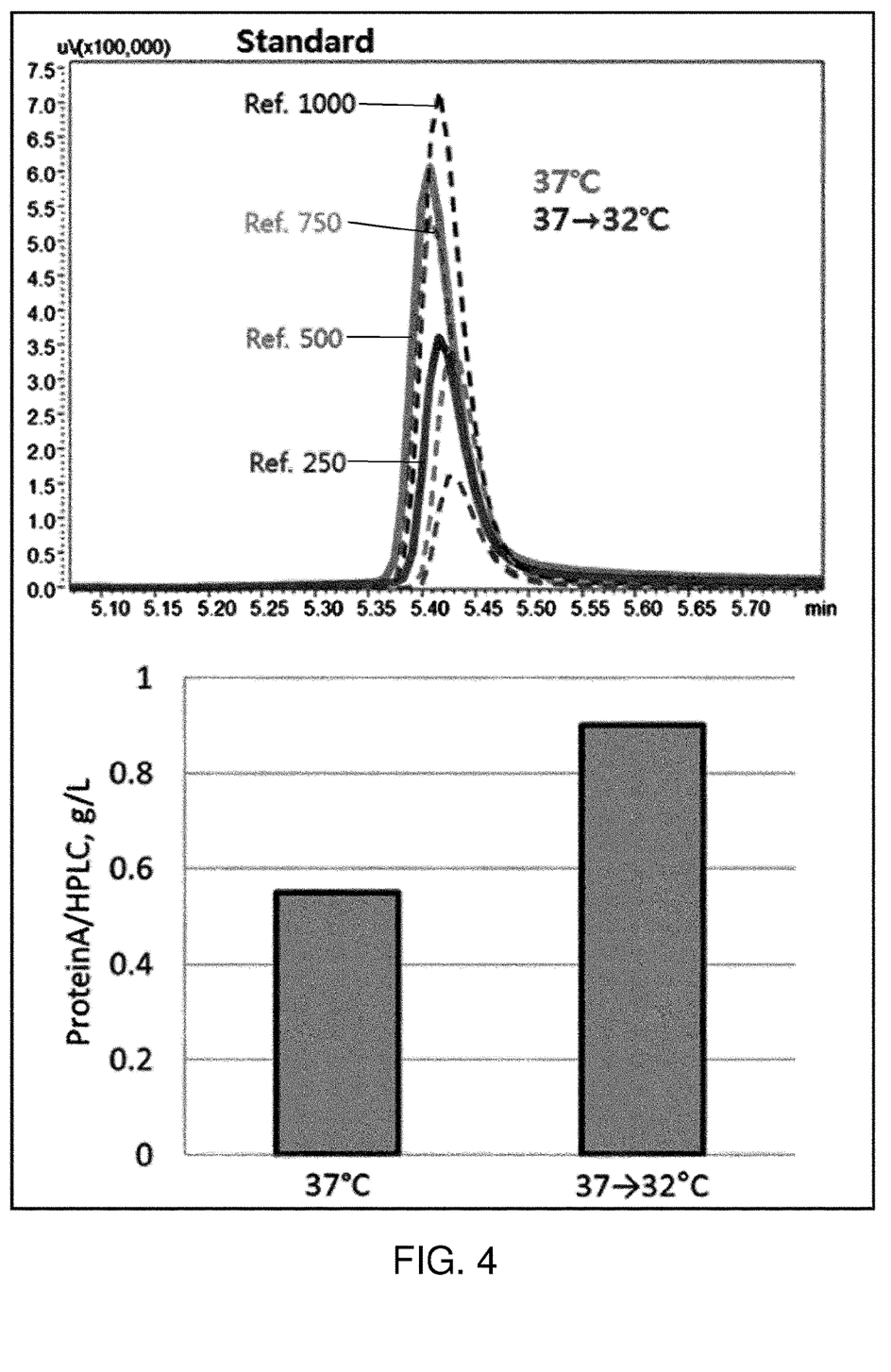
FIG. 4 is a graph analyzing a change in expression level according to the culture temperature of cells, which produce aflibercept, by high performance liquid chromatography (HPLC).

As illustrated in FIG. 1, cells grown in a flask at a lower temperature than the typical culture temperature exhibited a higher viability than cells continuously cultured at 37.0° C. (control) and the culture period was extended accordingly, and as a result, the expression level of the protein was increased as illustrated in FIG. 4. In contrast, as illustrated in FIGS. 2 and 3, cells grown in a flask at a lower temperature than the typical culture temperature do not affect the IVC number and the total amount of protein expressed (PV=culture volume×expression level) such that the specific production rate was not increased.

In another preferred exemplary embodiment of the present invention, cells overexpressing recombinant aflibercept were cultured at a temperature of 37.0° C. from the culture initiation date until a temperature change, for 2 days until the density of cells in a flask reached $8\times10^6$ cells/ml. Thereafter, the cells were fed-batch cultured according to the supply schedule in Table 1 at a decreased culture temperature of 30.0° C., 32.0° C. or 34.0° C.

Figure 5:
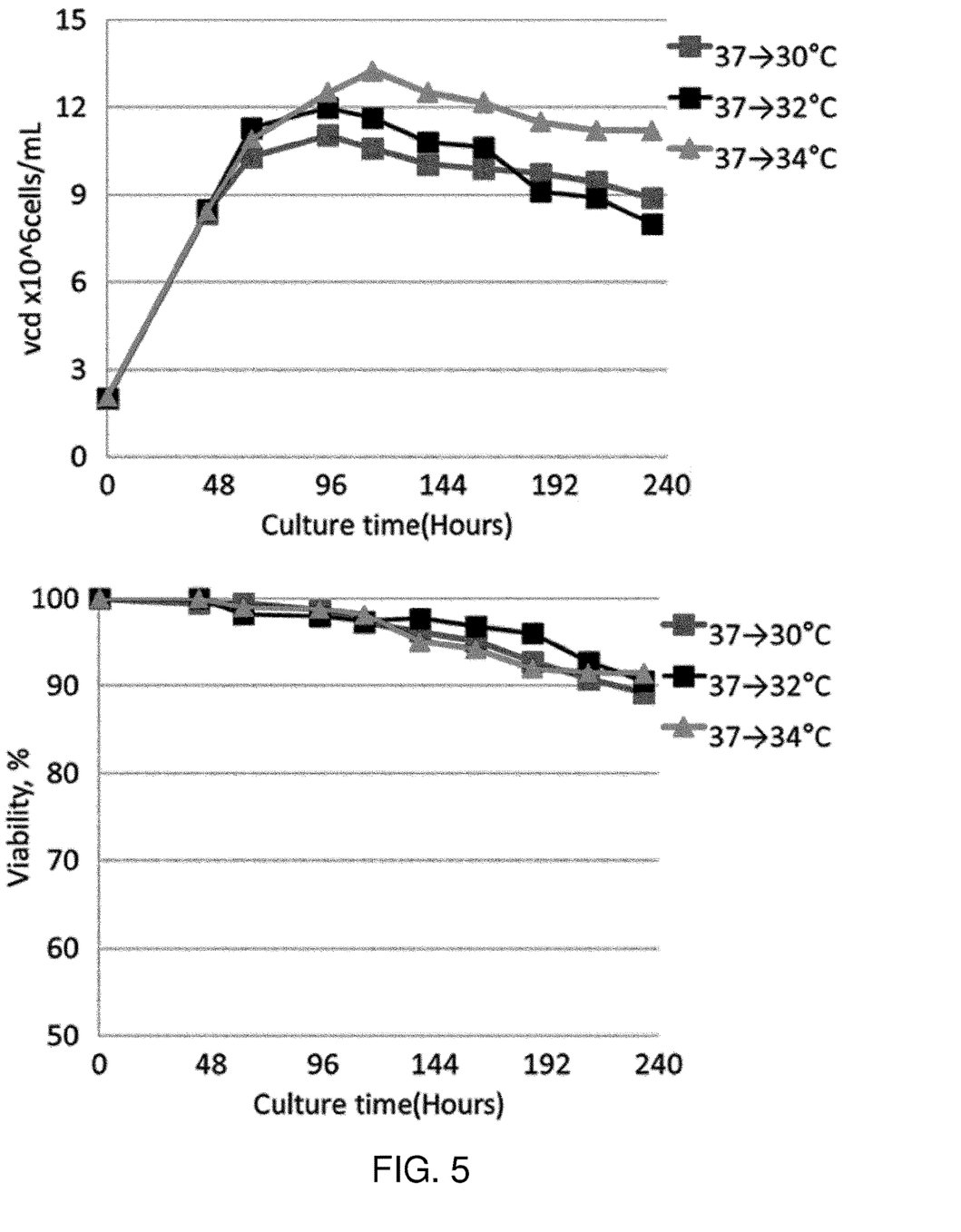
FIG. 5 is a graph analyzing a change in cell growth and cell viability according to a low culture temperature of cells, which produce aflibercept.
Figure 6:
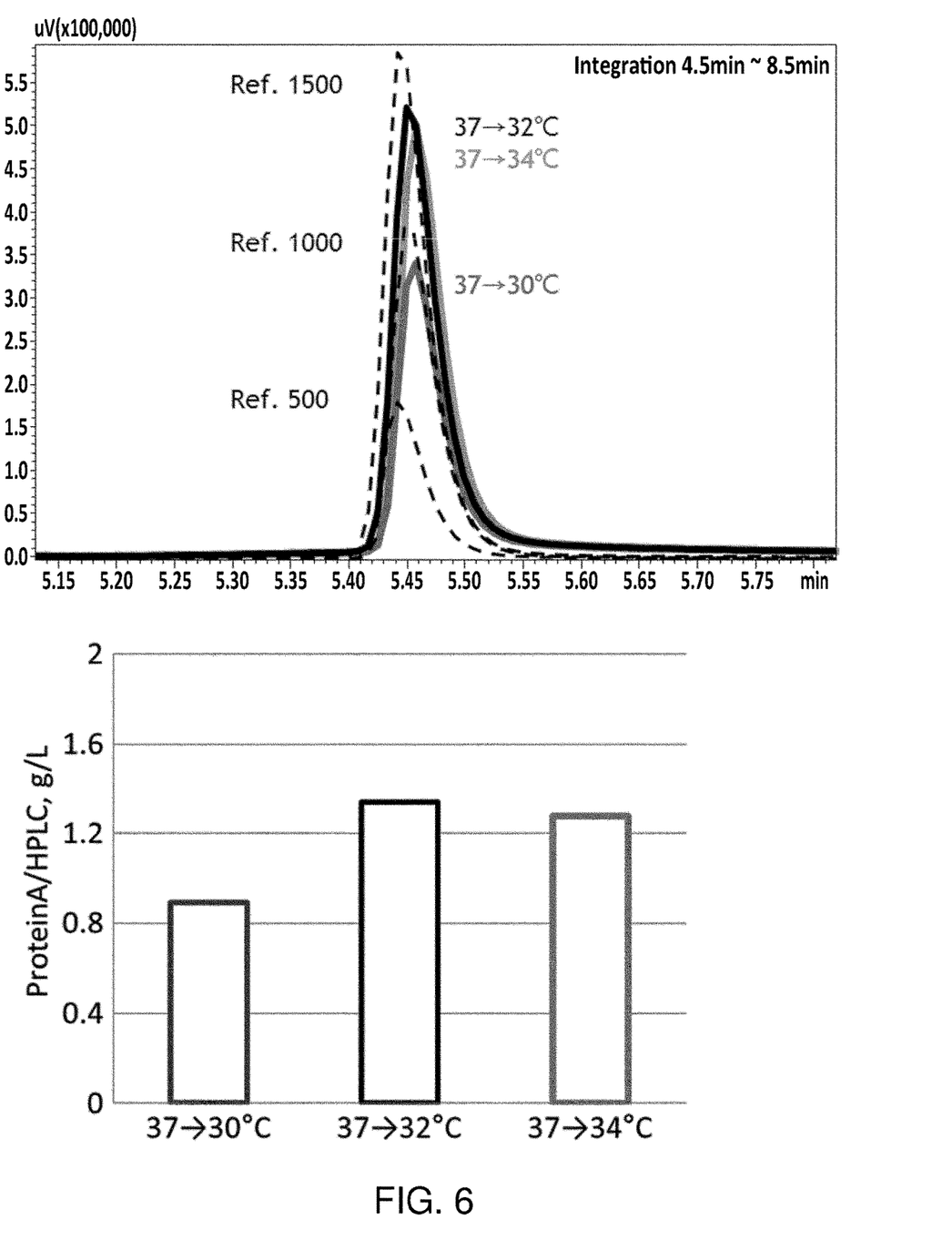
FIG. 6 is a graph analyzing a change in expression level according to a low culture temperature of cells producing aflibercept, by HPLC.

As illustrated in FIG. 5, the cell concentration in the culture at a culture temperature lowered to 34.0° C. in the flask was increased as compared to those at the other temperatures, but as illustrated in FIG. 6, an increase in expression level of the protein was the highest in the culture at a culture temperature lowered to 32.0° C.

In still another preferred exemplary embodiment of the present invention, the culture temperature from the culture initiation date until the temperature change was set to 37.0° C. to culture cells overexpressing recombinant aflibercept, for 1 day or 2 days until the density of cells in a bioreactor reached $4\times10^6$ cells/ml or $8\times10^6$ cells/ml. Thereafter, the cells were fed-batch cultured according to the supply schedule in Table 1 at a decreased culture temperature of 32.0° C. The pH of the culture broth in the bioreactor is different depending on the cell to be cultured, but generally, the pH may be 6.8 to 7.6, preferably 6.8 to 7.4. Further, dissolved oxygen (DO) in the culture broth in the bioreactor is generally 20% to 60%, preferably 30% to 50%, and more preferably 40%.

Figure 7:
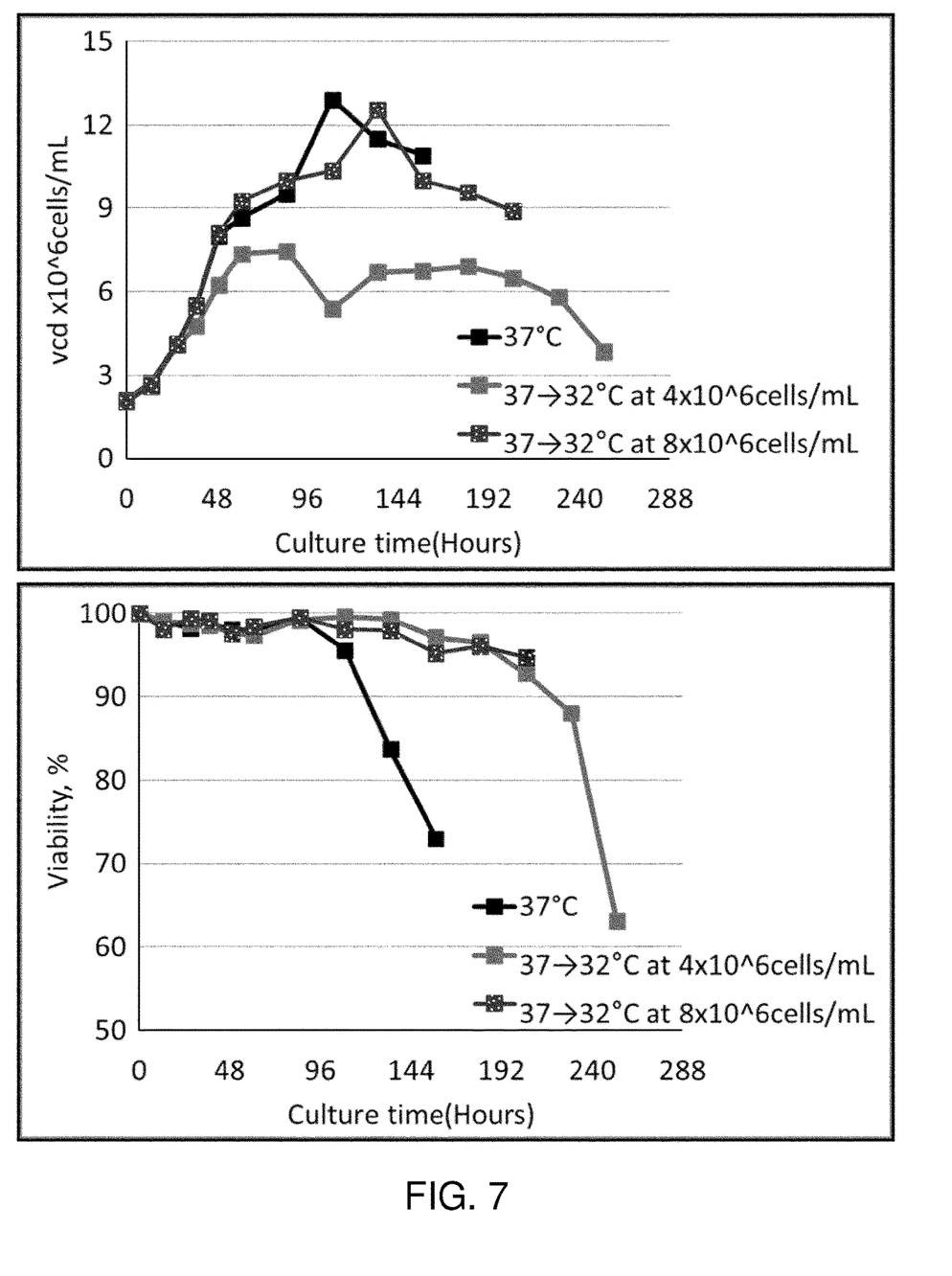
FIG. 7 is a graph analyzing a change in cell growth and cell viability according to the culture temperature of cells producing aflibercept, in a 2 L bioreactor.
Figure 8:
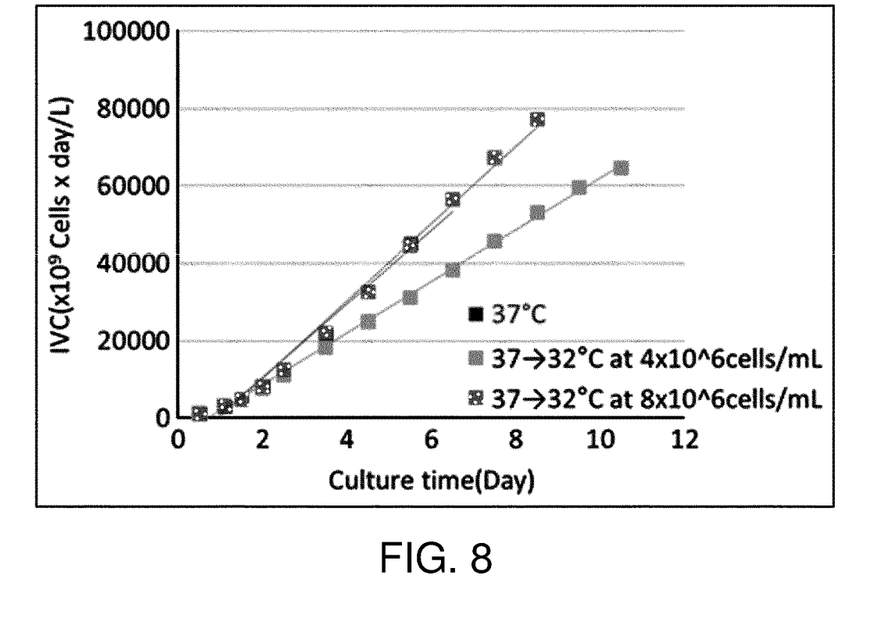
FIG. 8 is a graph showing integrated viable cell numbers (Y-axis; IVC [normalized $10^9$ cells×day/L]) producing aflibercept in a 2 L bioreactor, normalized to IVC, over time (X-axis; culture time [day]).
Figure 9:
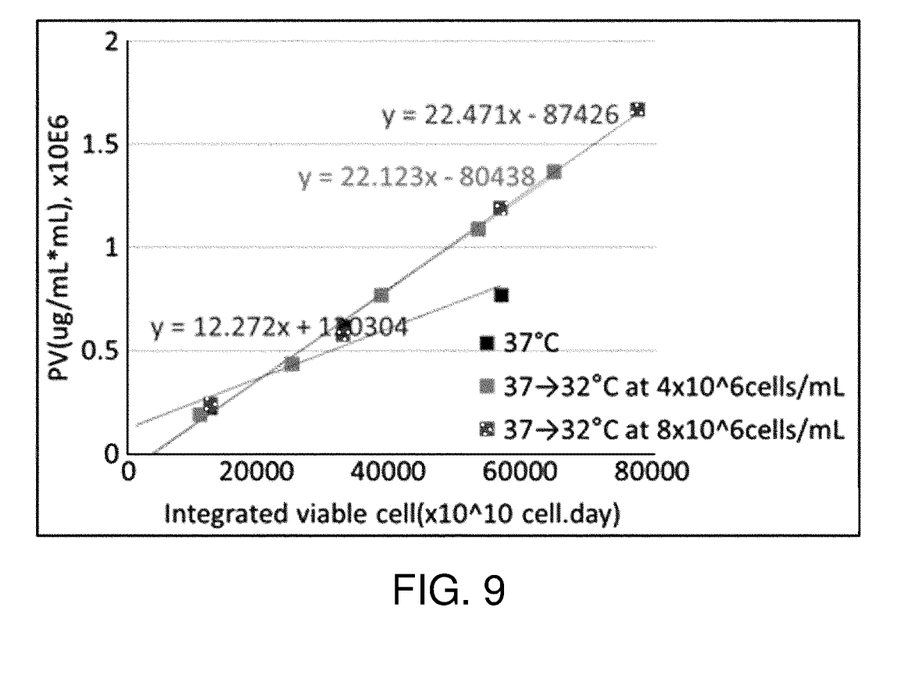
FIG. 9 is a graph showing a change in specific production rate according to the culture temperature of cells producing aflibercept, in a 2 L bioreactor.
Figure 10:
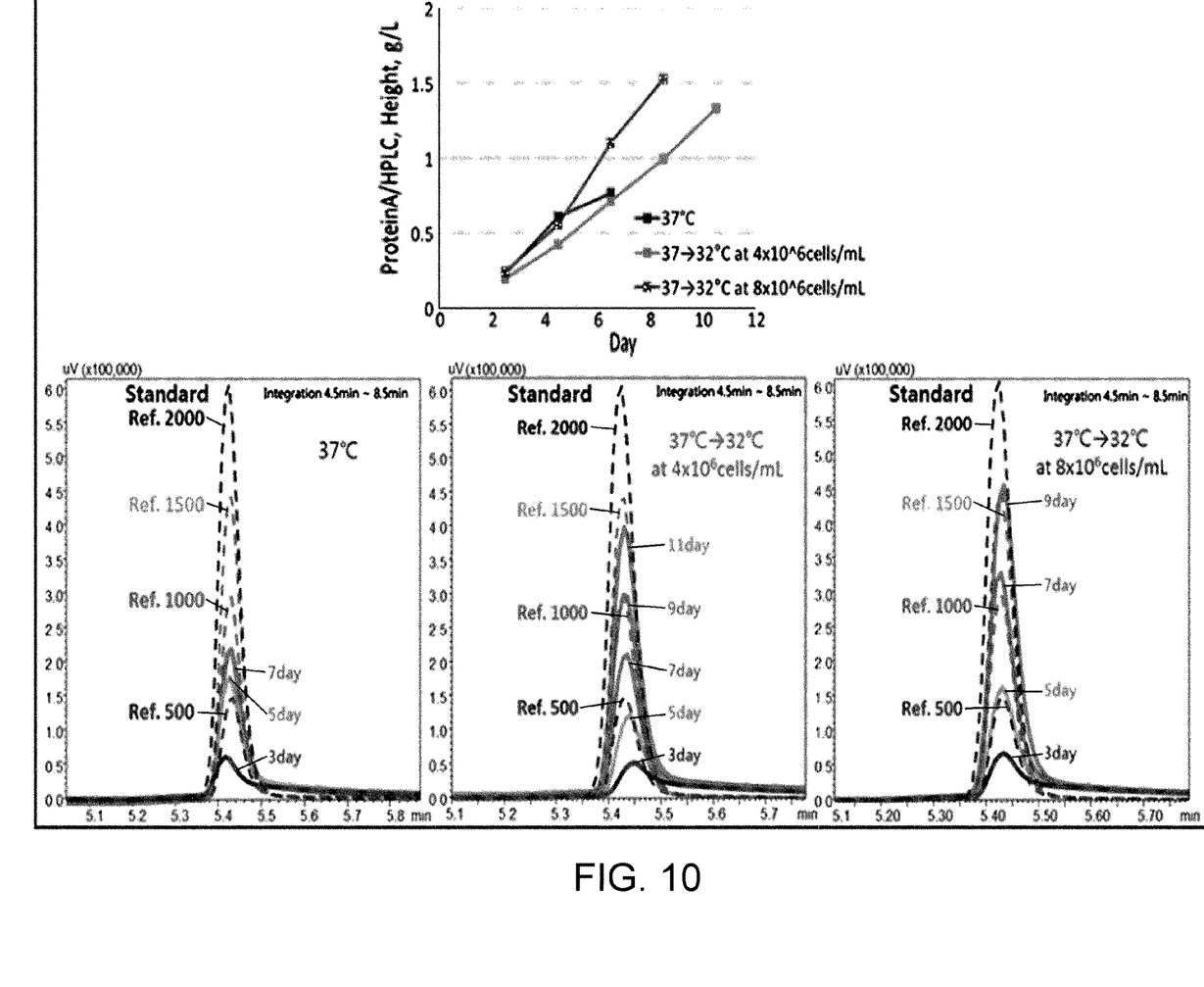
FIG. 10 is a graph analyzing a change in expression level according to the culture temperature of cells producing aflibercept, in a 2 L bioreactor by protein A-HPLC.
Figure 11:
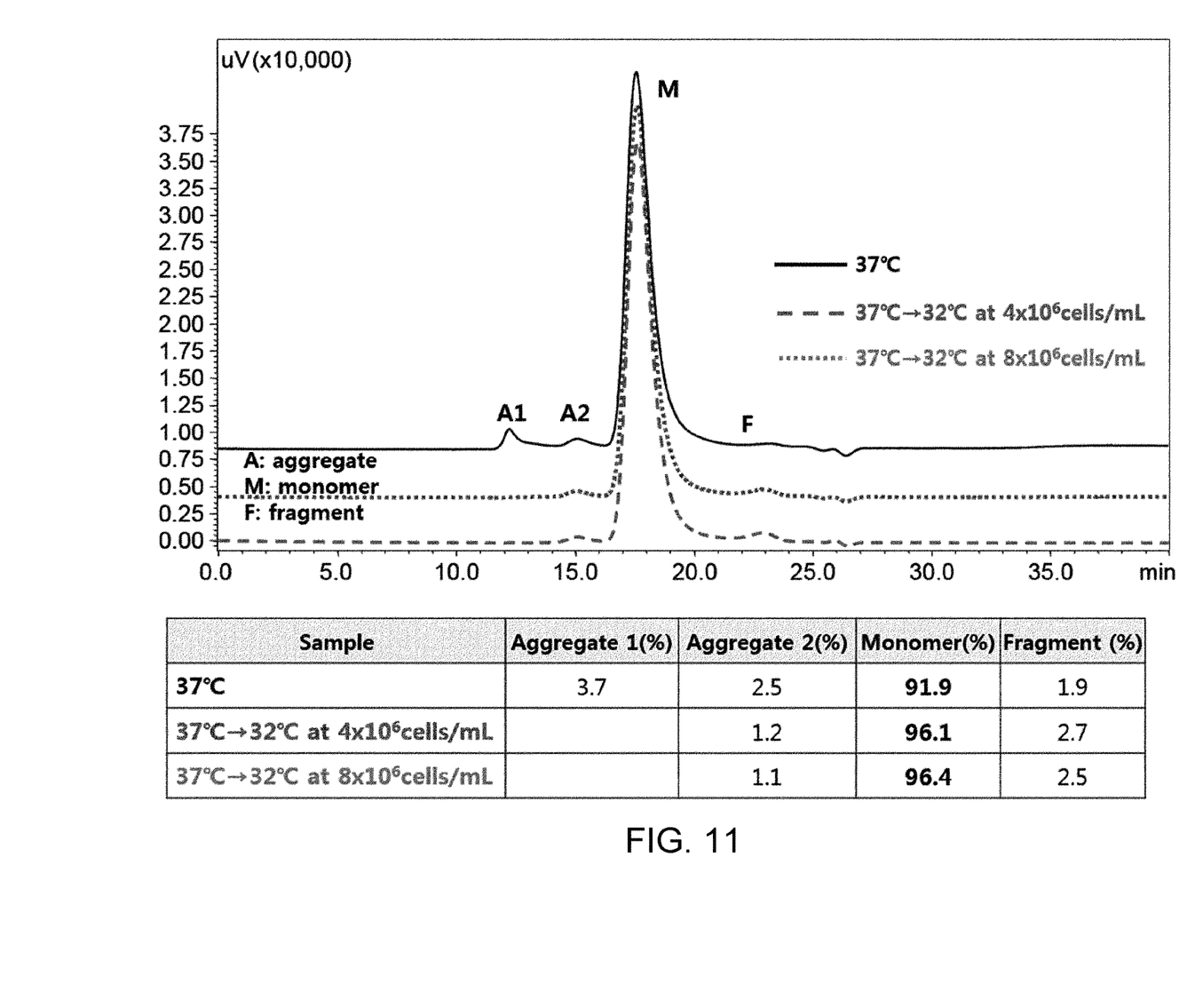
FIG. 11 is a graph analyzing a change in aggregated protein according to the culture temperature of cells producing aflibercept, in a 2 L bioreactor by size exclusion-high performance liquid chromatography (SE-HPLC).

Unlike the flask culturing (Erlenmeyer flask), cells cultured until a cell density of $8\times10^6$ cells/ml at the typical culture temperature (37.0° C.) by using a bioreactor and then at a culture temperature lower than the typical culture temperature did not affect the IVC number as illustrated in FIG. 8. However, as illustrated in FIG. 9, the specific production rate was increased due to the increase in total amount of protein expressed (PV=culture volume×expression level), and as illustrated in FIG. 7, the culture period was increased, and as a result, the expression level of the protein was increased as illustrated in FIG. 10. Further, as illustrated in FIG. 11, it was confirmed that less aggregates were generated, and the monomer purity was increased.

Accordingly, the method for producing a fusion protein having an IgG Fc domain according to the present invention may increase the productivity of the fusion protein by increasing growth and viability of cells producing the fusion protein having an IgG Fc domain, through optimization of the cell culture conditions.

Further, the method for producing a fusion protein having an IgG Fc domain according to the present invention may provide a fusion protein having an improved quality by improving a method for culturing mammalian cells to increase the productivity of the fusion protein and inhibit aggregate generation which affects the quality of the fusion protein.

The method of the present invention is characterized by increasing productivity of a desired protein and inhibiting aggregate ingredient generation when preparing the fusion protein by culturing cells producing the desired protein. Accordingly, the method may help improve the productivity of aflibercept, which is a protein in which a ligand binding portion of an anti-VEGF receptor is fused to an Fc region of the IgG1, and improve purification processes by inhibiting aggregate ingredient generation.

The present invention also provides a method for preparing a target protein, the method including: culturing cells producing the target protein through the above-described production method.

The method for producing a target protein according to the present invention may additionally include a process of recovering the target protein from a culture broth in which the cells producing the target protein were cultured.

A target protein prepared by the method for preparing the target protein may be a therapeutic protein, and the prepared therapeutic protein may be provided as a pharmaceutical composition together with a pharmaceutically acceptable carrier.

The pharmaceutical composition of the present invention may be prepared by using a pharmaceutically suitable and physiologically acceptable adjuvant in addition to an active ingredient, and a soluble agent such as an excipient, a disintegrant, a sweetening agent, a binder, a coating agent, a swelling agent, a lubricant, a slip modifier or a flavoring agent may be used as the adjuvant. The pharmaceutical composition of the present invention may be formulated by additionally including one or more pharmaceutically acceptable carriers in addition to an active ingredient for administration. In a composition formulated as a liquid solution, as a pharmaceutically acceptable carrier suitable for sterilization and a living body, it is possible to use a saline solution, sterilized water, Ringer's solution, a buffered saline solution, an albumin injection solution, a dextrose solution, a maltodextrin solution, glycerol, ethanol, and a mixture of at least one thereof, and other typical additives, such as an antioxidant, a buffering solution, and a bacteriostatic agent may be added, if necessary. Further, the composition may be formulated into a dosage form for injection such as an aqueous solution, a suspension, and an emulsion, a pill, a capsule, a granule or a tablet by additionally including a diluent, a dispersant, a surfactant, a binder, and a lubricant.

The pharmaceutical composition of the present invention may be administered to a mammal including a human via various routes according to the type of therapeutic protein prepared. For example, the pharmaceutical composition may be orally or nonorally administered, and a nonoral administration method may be, but is not limited to, intravenous, intramuscular, intraarterial, intramedullary, intradural, intracardiac, percutaneous, subcutaneous, intraperitoneal, intranasal, enteral, topical, sublingual, rectal, or intravitreal administration.

A suitable administration amount of the pharmaceutical composition of the present invention may vary depending on factors such as formulation method, administration method, the age, body weight, sex or disease condition of a patient, diet, administration time, administration route, excretion rate and response sensitivity, and a doctor with ordinary skill may easily determine and prescribe an administration amount effective for a desired therapy or prophylaxis.

Hereinafter, the present invention will be described in more detail through Examples of the present invention. However, the Examples are provided for exemplifying the present invention, and the scope of the present invention is not limited thereby.

EXAMPLES

Preparation Example

Preparation of Vector and Cell Line Expressing Recombinant Aflibercept

Recombinant aflibercept was cloned as a fusion protein by using a modified vector in which shGH, His tag, and TEV sites were removed from pSGHV0 (GenBank Accession No. AF285183), and the recombinant aflibercept was extracellularly secreted by using an intrinsic signal sequence of the protein.

Further, a GS system was introduced as a selection marker for constructing a cell line (stable cell line) constantly expressing the fusion protein, and for this purpose, a mouse glutamine synthetase gene was inserted into the vector. To increase the expression level, a Kozac sequence was additionally inserted into the signal sequence. And then, a stable cell line was obtained by introducing the thus-prepared clone into a CHO-K1 cell line (ATCC, Cat.CCL-61) and selecting methionine sulphoximine (MSX). However, a person skilled in the art may appropriately select typically used vectors and cell lines according to the given circumstances and apply them accordingly.

Example 1

Confirmation of Effects of Culture at Decreased Temperature on Cell State and IgG Fc Fusion Protein Production Cells overexpressing recombinant aflibercept prepared in the Preparation Example were inoculated into a medium supplemented with a plant-derived hydrolysis protein at the same concentration and conditions in two 125-mL Erlenmeyer flasks, and were shake-cultured in a $CO_2$ incubator at 37.0° C. The cells were grown by batch culture, and then fed-batch cultured by lowering the temperature to 32.0° C. when the cell concentration was about $8 \times 10^6$ cells/mL. The supply schedules for the experimental conditions are summarized in the following Table 1. A volume of the fed-batch feed is described as a percentage of the culture starting volume in a bioreactor. The levels of viable cell number, cell viability, expression and specific production rate were measured by taking cell samples from the culture every day. "Integrated viable cell number" or Integral viable cell (IVC)" means an average density of viable cells over the course of the culture multiplied by the culture period. When the amount of the produced protein was proportional to the number of viable cells present over the course of the culture, the integrated viable cell density was used to estimate the amount of protein produced over the course of the culture. The IVC was calculated by measuring the number of viable cells using a cell density test in which the viable cells are stained with trypan blue and measured under a microscope, and was normalized to IVC. The IVC was determined by calculating the arithmetic mean of the harvest date integrated viable cell densities for all experimental conditions tested. The expression level was measured by Protein A-HPLC, and the specific production rate was calculated.

TABLE 1

| Experimental conditions | 37.0° C. | 37.0→32.0° C. |
|---|---|---|
| Day 2 | 2.86% | 2.86% |
| Day 3 | 2.86% | 2.86% |
| Day 4 | 2.86% | 2.86% |
| Day 5 | 2.86% | 2.86% |
| Day 6 | 2.86% | 2.86% |
| Day 7 | 2.86% | 2.86% |
| Day 8 | 2.86% | 2.86% |

As a result, the specific production rate was not increased because cells cultured at a low temperature in the 125-mL Erlenmeyer flask did not affect the IVC number and the total amount of the expressed protein (PV=culture volume×expression level) (FIGS. 2 and 3). However, when cells were grown at a low temperature, the culture period and the expression level increased (FIG. 4) due to a higher cell viability (FIG. 1).

Example 2

Identification of Optimal Temperature Change Based on Expression Level of IgG Fc Fusion Protein Cells overexpressing recombinant aflibercept prepared in the Preparation Example were inoculated into a medium supplemented with a plant-derived hydrolysis protein at the same concentration and conditions in three 125-mL Erlenmeyer flasks, and were shake-cultured in a $CO_2$ incubator at 37.0° C. The cells were grown by batch culture, and then, when the cell concentration was about $8 \times 10^6$ cells/mL, fed-batch cultured at a decreased temperature of 30.0° C., 32.0° C., or 34.0° C., respectively. The supply schedules for the experimental conditions were as described in Table 1 of Example 1. Various states of the cells were measured as described in Example 1.

As a result, for cells cultured at a low temperature of 34.0° C., an increase in cell concentration was highest without any change in viability (FIG. 5). However, an increase in expression level of the cells cultured at a low temperature of 32.0° C. was highest as compared to those at the other temperatures (FIG. 6).

Example 3

Bioreactor Confirmation Experiment

Cells overexpressing recombinant aflibercept prepared in the Preparation Example were inoculated into a plant-derived feed medium in a New Brunswick Scientific (NBS) bioreactor and were stirred at a pH of 6.8 to 7.4 and a rate of 80 rpm. When the bioreactor reached a cell concentration of $4 \times 10^6$ cells/mL or $8 \times 10^6$ cells/mL on Day 1 or Day 2, the cells were cultured by changing the temperature from 37.0° C. to 32.0° C. The supply schedules for the experimental conditions were as described in Table 1 of Example 1. Various states of the cells were measured as described in Example 1.

As a result, unlike the 125-mL Erlenmeyer flask culturing, when the culture temperature was lowered at $8 \times 10^6$ cells/mL, the cultured cells did not affect the IVC number, the specific production rate was increased due to an increase in total amount of protein expressed (PV=culture volume× expression level), and the expression level was increased due to an increase in culture period (FIGS. 7 to 10). A protein was isolated by the Protein A column from the sample cultured under the above-described temperature conditions and was analyzed by SE-HPLC. From the result obtained by the SE-HPLC analysis, a monomer ratio was calculated, and ratios of aggregates which are polymer impurities and fragments which are low-molecular impurities were calculated. As a result of the experiment, it could be confirmed that in the culture at the decreased temperature, less aggregates were generated, and as a result, the monomer purity was increased (FIG. 11).

These results prove that through the method for producing a protein in which a soluble extracellular domain of a VEGF receptor and a human IgG Fc domain are fused according to the present invention, aflibercept, which is a representative of the fusion protein, can be produced at high quality due to inhibited aggregate generation, and productivity can also be increased due to a significant increase in expression level through the culture at the decreased temperature.

In the production of the fusion protein through the cell culture, the culture conditions simultaneously satisfying the quality and productivity of the protein are different depending on the type of protein, so that many trials and errors are needed to find optimal conditions. As proved in the Examples, the method for producing a fusion protein according to the present invention is optimized for the production of a protein in which a soluble extracellular domain of a VEGF receptor and a human IgG Fc domain are fused (for example, aflibercept), and when the type of protein varies, the productivity and quality of the corresponding protein may significantly vary. Accordingly, when the type of target protein to be produced varies, a process of re-establishing optimal conditions for improving quality and productivity and verifying the optimal conditions will be essentially required.

The above-described description of the present invention is provided for illustrative purposes, and a person skilled in the art to which the present invention pertains will understand that the present invention can be easily modified into other specific forms without changing the technical spirit or essential features of the present invention. Therefore, it should be understood that the above-described Examples are illustrative only in all aspects and are not restrictive.

The method for producing a protein in which a soluble extracellular domain of a VEGF receptor and a human IgG Fc domain are fused as provided by the present invention additionally includes a step of culturing cells producing the fusion protein at a decreased culture temperature, thereby increases fusion protein productivity by increasing cell growth and cell viability and improves quality by inhibiting the generation of aggregates of the fusion protein, and thus can prepare and supply the fusion protein in large amounts.

Further, a protein produced by the production method of the present invention is a therapeutic protein and can be used to provide a pharmaceutical composition suitable for the therapeutic purpose, and thus is highly industrially applicable.

The invention claimed is:

1. A method for producing a fusion protein in a cell culture, comprising:
   a) culturing cells capable of producing the fusion protein at a temperature range of 33° C. to 38° C.; and
   b) culturing the cells at a temperature range of 28° C. or greater and less than or equal to 35° C. when a cell density reaches $4\times10^6$ cells/ml to $1\times10^8$ cells/ml, wherein the temperature the cells are cultured in b) is lower than the temperature the cells are cultured in a) in order to increase an expression level of the fusion protein compared to culturing the cells without the temperature range of b) being lower than the temperature the cells are cultured in a), and
   wherein the fusion protein comprises a soluble extracellular domain of a vascular endothelial growth factor (VEGF) receptor and a human immunoglobulin G (IgG) Fc domain, wherein a sum of a culture period of a) and b) is 3 days or more.

2. The method of claim 1, wherein the fusion protein prepared by the method is a fusion protein with a reduced amount of aggregates compared to a fusion protein produced by culturing the cells without the temperature range of b) being lower than the temperature the cells are cultured in a).

3. The method of claim 1, wherein the cell culture is any one or more selected from a group consisting of batch culture, repeated batch culture, fed-batch culture, repeated fed-batch culture, continuous culture, and perfusion culture.

4. The method of claim 3, wherein the cell culture is fed-batch cell culture.

5. The method of claim 1, wherein the cell is a mammalian cell.

6. The method of claim 5, wherein the mammalian cell is a Chinese hamster ovary (CHO) cell.

7. The method of claim 6, wherein the CHO cell is a cell line of any one selected from a group consisting of DG44, DXB-11, K-1 and CHO-S.

8. The method of claim 1, wherein the temperature range of b) is in a range of 30° C. to 35° C.

9. The method of claim 1, wherein a culture period of a) is 1 to 5 days.

10. The method of claim 1, wherein a culture period of b) is 2 to 15 days.

11. The method of claim 1, wherein the soluble extracellular domain of the VEGF receptor comprises immunoglobulin-like domain 2 of a first VEGF receptor and immunoglobulin-like domain 3 of a second VEGF receptor, wherein the first and second VEGF receptor are different.

12. The method of claim 1, wherein the produced fusion protein is a therapeutic protein.

13. The method of claim 1, further comprising a process of recovering the fusion protein from a culture broth in which the cells were cultured.

14. The method of claim 13, wherein the fusion protein is a therapeutic protein.

* * * * *